United States Patent [19]
DeRossett et al.

[11] Patent Number: 4,624,666
[45] Date of Patent: Nov. 25, 1986

[54] CHANNELED NAPKIN WITH DRY COVER

[75] Inventors: Edmund Z. DeRossett, Mercerville; Frederick F. Gentzel, Ringoes, both of N.J.

[73] Assignee: Personal Products Company, Milltown, N.J.

[21] Appl. No.: 632,754

[22] Filed: Jul. 20, 1984

[51] Int. Cl.⁴ .............................................. A61F 13/16
[52] U.S. Cl. .................................. 604/366; 604/365; 604/378; 604/379; 604/380
[58] Field of Search ............... 604/365, 366, 378, 379, 604/380

[56] References Cited

U.S. PATENT DOCUMENTS

| 3,441,023 | 4/1969 | Rijssenbeck | 604/378 X |
| 3,881,490 | 5/1975 | Whitehead et al. | 604/380 X |
| 4,029,101 | 6/1977 | Chesky et al. | 604/378 X |
| 4,077,410 | 3/1978 | Butterworth et al. | 604/366 |
| 4,184,498 | 1/1980 | Franco | 604/379 X |
| 4,443,512 | 4/1984 | Delvaux | 604/379 X |

Primary Examiner—Earl Nielsen
Attorney, Agent, or Firm—Jason Lipow

[57] ABSTRACT

A sanitary napkin is provided which comprises a cover with clean and dry properties in combination with the fluid transport properties of an impressed channel. The napkin comprises an absorbent core having impressed into its body facing side at least one elongated channel. A hydrophobic, body fluid pervious, cover overlies said body facing side and said channel and said cover extends into the channel and is adhered to the channel bottom.

15 Claims, 7 Drawing Figures

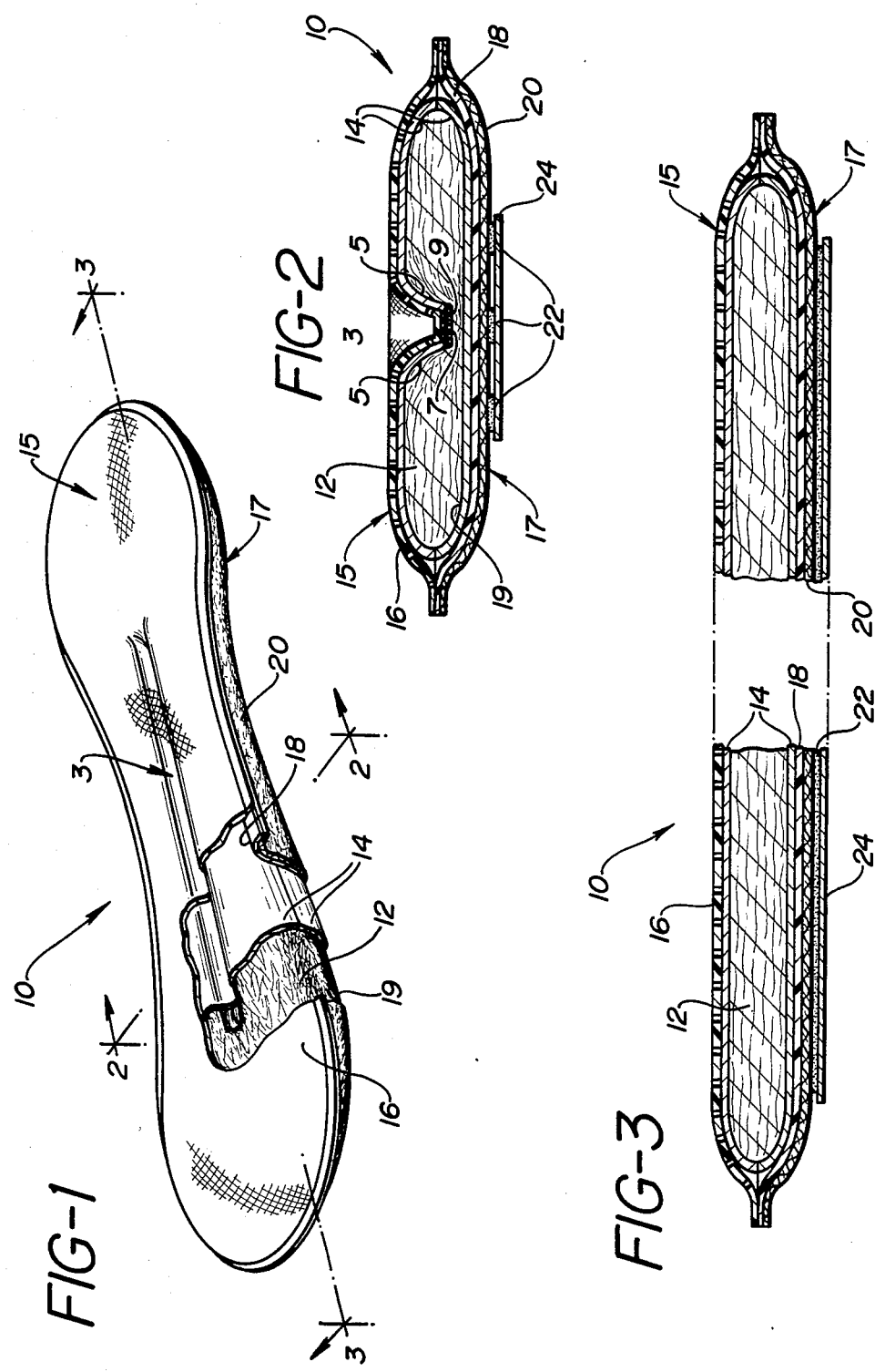

CHANNELED NAPKIN WITH DRY COVER

BACKGROUND OF THE INVENTION

This invention concerns providing a sanitary napkin which is so constructed as to incorporate a fluid distributing channel impressed into the absorbent element of the napkin and is provided with a cover for the body facing side which cover remains clean and dry after deposition of body fluid thereon. In particular, this invention relates to a sanitary napkin so constructed as to fully utilize the fluid distribution properties of a channel without sacrificing the clean and dry attributes of the cover.

For many years sanitary napkins have comprised a loosely associated pad or batt of absorbent fibers such as wood pulp or rayon, of generally uniform density, enveloped in a body fluid permeable cover and provided, on the garment side thereof, with a fluid impermeable barrier layer. While such napkins have functioned more or less satisfactorily, it has been long recognized that the uniform density pad does not allow for full utilization of the absorption capacity of the pad and instead the napkins tend to fail, i.e., leak body fluids onto the outer garment facing surfaces, before the pad is fully saturated.

Recent prior suggestions have been made to obviate this problem, typical of which is that disclosed in U.S. Pat. No. 4,184,498 issued to Pierre Franco on Jan. 22, 1980. As disclosed therein, a pad is provided with a densified longitudinally extending centrally positioned channel impressed into the body facing side and surrounded by less dense peripheral portions of the pad. The central channel serves to direct fluid deposited centrally on the pad in a generally longitudinal direction and thereby make better use of the absorbent capacity of the pad. In commonly assigned U.S. Ser. No. 530,320 filed on Sept. 8, 1983 a similarly channeled pad for a sanitary napkin is disclosed which pad is provided with a density gradient with the density varying from a low density in a central portion of the pad to a rapidly increasing high density at the extreme peripheral portions of the pad. This described density pattern again provides improved fluid transport to more fully utilize the absorbent capacity of the pad.

In addition to the problem of fluid transport, the art has recently been concerned with the desirable feature of providing a cover for a sanitary napkin which, after deposition of body fluid, is capable of maintaining a clean and dry appearance. Accordingly, sheet materials for use as the cover or facing for sanitary napkins have been selected to be not only pervious to body fluid but also not wettable by such fluid, i.e., hydrophobic. Such hydrophobic facing materials have several advantages in that they remain relatively dry and hence more comfortable in use. Additionally, by not wetting they remain free of stain on their exterior surface. The art is now replete with suggestions for utilizing hydrophobic facings in body fluid absorbent products. For example, in U.S. Pat. Nos. 3,695,269; 4,041,951; and 4,391,869; it has been suggested that nonwoven fabrics comprised of hydrophobic fibers be employed as the facing in absorbent products. In U.S. Pat. Nos. 2,992,644; 3,814,101; and 4,324,246; it is suggested that the facing comprise a continuous sheet of hydrophobic polymeric material rendered permeable to body fluid by being provided with apertures.

In a commonly assigned U.S. patent application filed on this day bearing Ser. No. 632,753, a particularly useful facing is suggested, which is not only substantially nonwettable and fluid pervious but which also greatly enhances the clean and dry appearance of the product after it has absorbed body fluids. This facing comprises a continuous sheet of a polyolefin incorporating therein from 5 to 12 percent by weight of titanium dioxide and having apertures therethrough for the passage of body fluid. The open area of the apertures comprise from 1.3 to 35 percent of the total area intended for the passage of body fluids. The combination of prescribed open area and titanium dioxide content results in a facing which allows for the passage of fluids, remains dry, and moreover, appears clean and dry by masking the stain pattern on the underlying absorbent pad.

It can thus be seen that solutions have been presented for improving fluid transport in a pad and that solutions have been presented for providing a cover with a clean and dry appearance. Unfortunately, it has been discovered that when attempting to employ the suggested solutions to the two problems, (i.e., fluid transport and clean and dry appearance) in a single pad, unsatisfactory results are obtained. Specifically, when a cover such as that described in connection with above-referenced application, Ser. No. 632,753, is employed on a pad without a central channel, excellent clean and dry properties follow. On the other hand, when employing such a cover on a channeled product, while the majority of the body facing surface of the cover remains clean and dry and appears so to the user, the portion of the cover overlying the channel retains a small but measurable, apparent and undesirable quantity of body fluid.

Accordingly, there is a need to provide a napkin capable of combining the clean and dry aspects of a cover having such properties with the fluid transport properties of a channeled pad.

SUMMARY OF THE INVENTION

In accordance with this invention a napkin is provided which is so constructed as to take full advantage of a channeled pad, specifically the concommitant fluid transport properties of such a channeled pad, while employing a hydrophobic cover, taking full advantage of the dry and clean appearance of such cover.

Specifically, a sanitary napkin is provided which comprises an absorbent core having a body facing side, i.e., the side to be employed against the body for absorbing body fluid, and a garment facing side, i.e., the side opposite the body facing side, which garment facing side is generally worn against the crotch portion of the wearer's undergarment. Impressed into the body facing side of the absorbent core is at least one elongated channel having walls and a bottom for transporting body fluid generally in the elongated direction. The napkin is provided with a hydrophobic, body fluid pervious cover which overlies the body facing side of the core including its impressed channel. In accordance with this invention it has been discovered that in order to fully obtain the clean and dry aspect of such a hydrophobic cover, it is necessary to have such cover extend into the channel and adhere to the bottom of the channel. In contrast with the teachings herein, it has been discovered that if the cover merely overlies and spans the channel or is merely draped into the channel, the area of the cover overlying the channel remains wet to an observable and quantitatively ascertainable degree which is both functionally and aesthetically disadvantageous.

Depending upon the materials of construction for the cover and the absorbent core, the adherence of the cover to the bottom of the channel may be effected in various ways. For example, if the cover comprises a thermoplastic material, it is possible to gain such adherence by the application of heat or heat and pressure, i.e., auto heat bonding. Alternatively, the cover may be adhered to the bottom of the channel by employing an adhesive substance. In a preferred embodiment the adhesive substance is one that is adhesively activatable by the application of relatively low temperature heat.

The channel configuration may be varied considerably and the benefits described herein will still inure to these variations. Preferably the channel should extend generally in the longitudinal direction of the absorbent core although it should be understood that the elongated channel need not be strictly in the shape of a straight line, i.e., the channel may be arcuate, sinusoidal or otherwise curved provided a substantial portion of the channel extends generally in the longitudinal direction. Similarly more than one channel may be employed.

The hydrophobic cover is preferably a polymeric film material which is rendered fluid pervious by virtue of having apertures therethrough. Preferably such cover is the cover material described above in connection with the commonly assigned patent application Ser. No. 632,753 filed on this day.

BRIEF DESCRIPTION OF THE DRAWINGS

FIG. 1 is a perspective view of a sanitary napkin incorporating the teachings of this invention and illustrated with parts removed to show internal elements;

FIG. 2 is a transverse, cross sectional view of the napkin of FIG. 1 taken through line 2—2;

FIG. 3 is a longitudinal, cross sectional view of the napkin of FIG. 1 taken through line 3—3;

DETAILED DESCRIPTION OF THE INVENTION

Figure 4:
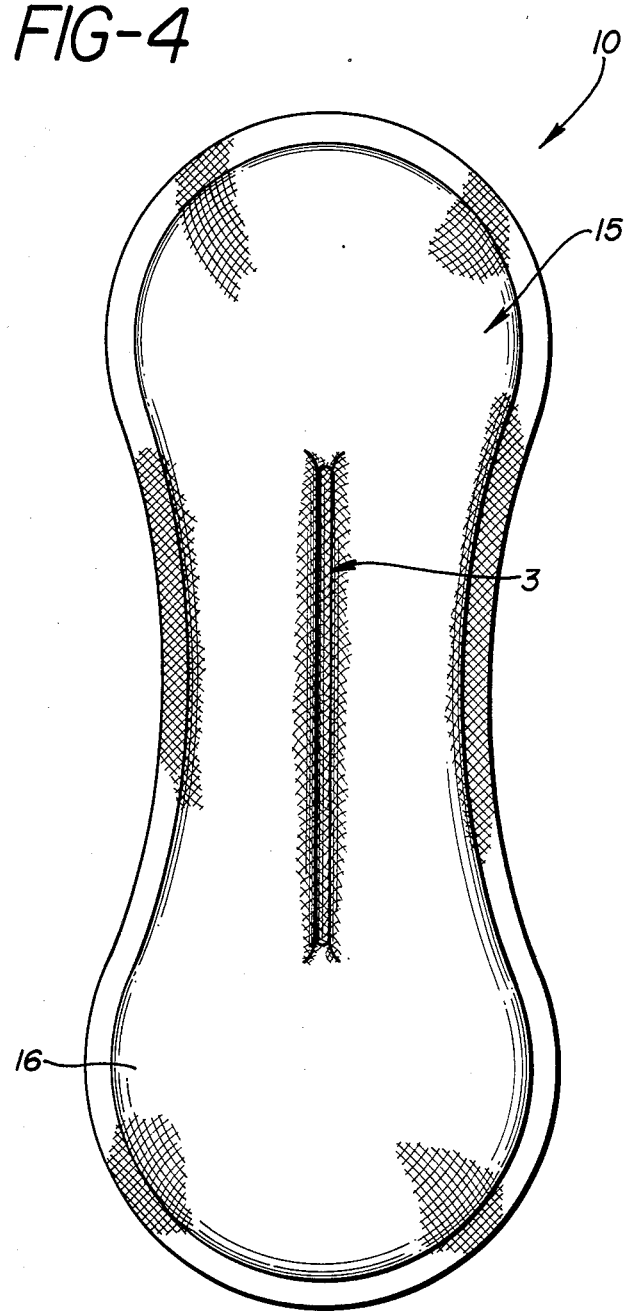
FIG. 4 is a plan view of the body facing side of the napkin of FIG. 1.

Referring now to FIG. 1, illustrated there in perspective view is a first sanitary napkin 10, incorporating the teachings of this invention. FIGS. 2, 3, and 4 illustrate the napkin 10 in transverse section, longitudinal section, and plan views, respectively.

The napkin 10 consists of a generally planar core or pad 12 of absorbent material which may be any such material suitable for use in sanitary napkins and may include, for example, loosely associated absorbent hydrophilic material such as cellulose fibers, e.g., wood pulp, regenerated cellulose or cotton fibers. Such fibers may be chemically or physically modified and the pad may include such fibers in combination with other materials, both natural and synthetic, such as hydrophilic foams, other hydrophilic polymers or the like.

The pad 12, as illustrated in FIGS. 1-3, is wrapped in a tissue wrap 14 which is provided to aid in holding the product together during manufacturing and to help retain the shape of the finished product.

Overlying the garment facing side 17 (the side worn away from the body of the user) of the pad 12 and at least a part of the edges 19 of the pad 12, is a body fluid impervious layer 18. The layer 18 is provided to preclude body fluid from passing onto an undergarment and may be constructed of any material suitable for this purpose. For example, the layer 18 may be a polymeric film such as polyethylene, polypropylene or cellophane or may be a normally fluid pervious material that has been treated to be impervious such as a fluid repellent paper or tissue. Advantageously, the layer 18 is a heat bondable material such as polyethylene which can be bonded to the facing layer 16 to completely enclose pad 12.

In a preferred configuration, layer 20, a nonwoven fabric constitutes the outer layer of the garment facing side of the napkin 10. This fabric outer layer is provided for aesthetic purposes and for its soft feel.

As best viewed in FIGS. 2 and 3, the garment facing side of the napkin is provided with pressure sensitive adhesive elements 22 for adhering the napkin to the crotch portion of the wearer's undergarment. As shown in this specific embodiment, these adhesive elements 22 are in the form of three longitudinally extending bands. The adhesive elements or bands are protected by a release strip 24 to avoid undesired adhesion prior to use.

Impressed into the body facing side 15 of pad 12 is an elongated channel 3 having walls 5 and a bottom 7. The channel 3 is centrally located on the body facing side 15 of the pad 12 with respect to the longitudinal and lateral ends thereof and extends longitudinally for a length equal to a substantial portion of the length of pad 12, i.e., at least 10 percent of the length of pad 12 and preferably, at least about 25 percent. Advantageously, the channel does not extend to the extreme transverse ends of the pad 12. As has been described above, the channel serves to transport body fluid, deposited on the body facing side of the napkin 10 and permeating to pad 12, in the elongated direction of the channel thereby more fully utilizing the absorbent capacity of pad 12. As shown best in FIG. 2, the channel depicted therein in transverse cross section has a generally U-shape although such other cross sectional shapes such as V-shaped or even W-shaped will suffice. While the width and depth of this channel are not critical so long as the channel is dimensioned to a degree sufficient to perform its fluid transport function, preferably the channel, at its widest part is from about 0.1 to about 3 cms. wide and at its deepest point from about 0.1 to about 1.5 cms. deep.

Overlying the body facing side 15 of pad 12 is a hydrophobic body fluid pervious cover 16. Preferably the cover 16 is a continuous sheet comprising a polyolefin and provided with apertures for allowing body fluids to pass therethrough and to reach and be held by the absorbent core e.g. pad 12. The art is now replete with teachings for preparing apertured sheets, such methods generally requiring first forming a nonapertured continuous film of the polyolefin and then aperturing the same by means of piercing, e.g., with needles or the like; embossing, followed by piercing; applying heat to weakened areas; stretching or otherwise deforming a selectively weakened film to open apertures in selected areas.

One particularly useful method is described in U.S. Pat. No. 3,137,746. Such method is generally described as the making of a net-like product by a process involving stretching a profiled polymer sheet, i.e., an embossed or debossed sheet.

The polymeric olefin employed in the facing material of this invention may be selected from the group consisting of polyethylene, polypropylene or copolymers thereof with the polyolefin of choice being high density polyethylene. Other polymers may be employed to enhance desired properties. For example, a particularly useful blend includes minor portions of a polymer containing an aryl group such as high impact polystyrene. Such a blend is describe in U.S. Pat. No. 4,135,021. As taught therein, the aryl group containing polymer may be present in such proportion as not more than 40% by weight and preferably not more than 20% by weight, e.g., 5-20% by weight.

In the aforementioned U.S. Pat. No. 4,135,021 it is taught that the material can contain up to 5% by weight of an inert delustering filler such as titanium dioxide, said to improve the appearance and splittability characteristics of the materials. In contrast to this teaching and as is taught in the above-referred copending patent application Ser. No. 632,753, it has been discovered that such a material is wholly inadequate to mask the underlying stain on the surface of the absorbent area of a body fluid absorbing product. Instead, the facing material of such a product should, in conjunction with a prescribed open area limitations be heavily loaded with titanium dioxide (or with a material having the equivalent opacifying properties). Such loading must be greater than 5% by weight although preferably less than 12% by weight. The upper limit of such loading is selected by the fact that beyond 12% by weight, titanium dioxide tends to separate out of the polymer mix during manufacture and hence higher loadings are impractical. Preferably, such loading should vary from about 7% to about 10% by weight.

As set out in the referred to patent application Ser. No. 632,753, to achieve the desirable masking effect, the high titanium dioxide loading must be coupled with a prescribed limited range of open area. As used herein open area is the total area of the apertures in the facing expressed as a percentage of the total area of the facing, as measured on the body facing side of the absorbent product. Clearly no open area at all will maximize the ability of the facing to mask the underlying stain. Needless to say, no open area will likewise preclude passage of body fluid into the absorbent area of the product and hence some open area must be provided. In U.S. Pat. No. 4,324,246, it is taught that such open area should be at least 35% and preferably at least 55%. It has been discovered that if such large open area is employed, the masking effect of the facing is greatly reduced, irrespective of the titanium dioxide loading, in that the underlying stain is clearly visible through the facing. Further, it has been discovered that such large open area is entirely unnecessary to obtain satisfactory transmission of the body fluid through the facing and into the core. Open areas of from about 15% to about 35% are wholly adequate to meet the body liquid transmission requirements of such products as full sized sanitary napkins and, in the case of products designed to meet low body liquid flow rates, such as mini pads, panty shields and the like, open areas as low as 1.3% are acceptable.

A cover of the kind described above provides great advantages with respect to the properties of nonwetting and masking of underlying stained areas and, in fact, such a cover serves such purposes, in the main, on the product of FIGS. 1-4. It has been discovered, however, that for that portion of the cover overlying the channel 3, heretofore, such cover portions would, after application of body fluid thereon, exhibit a detectable, measurable and undesirable wetness. This wetness is exhibited for example when the cover is merely wrapped around or laid over the product and sealed to the peripheral portion of the barrier layer 20 to envelop the channeled pad 12. Similarly, the cover wetness in the channel area is exhibited when the cover is laid over an unchanneled pad and the channel is then impressed into the pad. In this latter instance, while the portion of the cover overlying the channel is pushed to some degree into the formed channel, when pressure is released, without any positive steps to the contrary being taken, the relatively stiff cover material tends to separate from the channel bottom. Under such circumstances, again, the undesirable wetness is manifested.

In accordance with the teachings herein, it has been discovered that this problem may be obviated by taking positive steps to provide a napkin wherein the cover is positively adhered to the bottom of the channel. Such adherence may be accomplished by a variety of methods although, from the point of view of commercial practicality, some methods are more preferred than others.

For example, it is possible to choose as the cover material, a polymeric composition which upon application of heat will deform, soften and fuse to the pad material at the bottom of the channel, adhering thereto. Thus the cover may be placed over a channeled pad and a heated male member conforming to the general dimensions of the channel may press the cover into the channel and adhere the same to the bottom of the channel. Alternatively, the cover may be placed over an unchanneled pad and a similar heated male member may simultaneously form the channel in the pad and adhere the cover to the bottom of the channel. Such a method (referred to herein as autoheat bonding, i.e., without additional adhesives) can be effected with a polyethylene cover as has been described above and has the advantage of requiring no additional application of adhesive materials which can add to material and processing costs. On the other hand such a method must be carefully controlled in that application of heat at too high a temperature or for too long a time interval can totally melt the cover material and destroy its integrity or adhere to the processing equipment requiring disadvantagous down time or otherwise unnecessary clean up. For example, with polyethylene covers, the maximum temperature of the male member should be between 290° and 300° F. and not be applied to the cover for a time interval of more than 0.4 sec.

Another method is to provide an adhesive material such as an emulsion adhesive which may be applied to that portion of the cover overlying the channel. The cover is then pressed into the channel and after the adhesive sets, will adhere the cover to the bottom of the channel. A wide range of adhesives are suitable for this purpose and the problem of overheating referred to above is thus obviated. A drawback of such method is that the adhesive must set, i.e., generally, the dispersing medium must be evaporated from the system.

A preferred method for adhering the cover to the channel bottom is to employ the so-called hot melt adhesives for this purpose. Hot melt adhesives are materials which are solid and nontacky at room temperature but which, upon application of heat, become soft and tacky. Additionally, upon removal of a heat source, they rapidly cool and solidify to the nontacky condition. Hot melt adhesives are available to be adhesively activatable in a wide range of temperatures. Preferably, for use in this invention the hot melt adhesives should have an adhesively active temperature below the melting point of the cover material, i.e., at least two degrees Farenheit below such melting point and preferably at least four degrees below the melting point. For a polyethylene cover, for example, where the melting point is about 260° F., the hot melt adhesive composition should be adhesively active at a temperature of below 258° F. and preferably below 256° F., e.g., 255° F.

It is also important to select a hot melt adhesive which is not adhesively active at too low a temperature in that the product of this invention may be stored at relatively high temperature condition, particularly during the summer months. Accordingly, the hot melt adhesive should not be adhesively active at temperatures below about 140° F. and preferably should not be adhesively active at temperatures below 150° F.

A wide variety of hot melt adhesive compositions are currently available commercially and are suitable for use in connection with this invention. Such adhesives as have been successfully utilized may be described generally as poly(ethylene vinylacetate)/polystyrene compositions, atatic branched hydrocarbon polymers and polyvinyl acetate/polystyrene hydrocarbon block copolymer blends.

As is best illustrated in FIG. 2, the cover 16 is adhered at the bottom of the channel 7, utilizing hot melt adhesive 9. It will be understood that while FIG. 2 is being described herein in terms of hot melt adhesive as the adhering medium, the schematic drawing of the napkin, FIG. 2, would appear essentially the same if an emulsion adhesive or merely auto heat bonding were employed as the adhering method.

The adhesive 9 may be a continuous elongated element running the full length of the channel 3 or may be intermittent or only a fraction of the length of the channel. Good results have been obtained when as little as 0.001 grams of adhesive per linear inch of channel have been employed although it is preferable to use at least 0.0015 gram of adhesive per linear inch, i.e., 0.006 grams for a three inch long channel. In any event, no more than 0.01 gms/linear inch should be employed and preferably less than 0.005 gm/linear inch should be used.

In manufacturing the product, the hot melt adhesive may be applied to the bottom of the channel after it is formed. Alternatively, the adhesive may be applied to the pad (or tissue wrap) in the area where the channel is to be formed, the cover may be placed over the pad, the channeled formed and the cover adhered by use of a heated male member. In still another alternative, the hot melt adhesive may be applied to the cover at the area of the cover intended to overlie the channel in the finished product and the cover may be adhered by application of a heated male member. Again this male member may also serve to form the channel.

Figure 5:
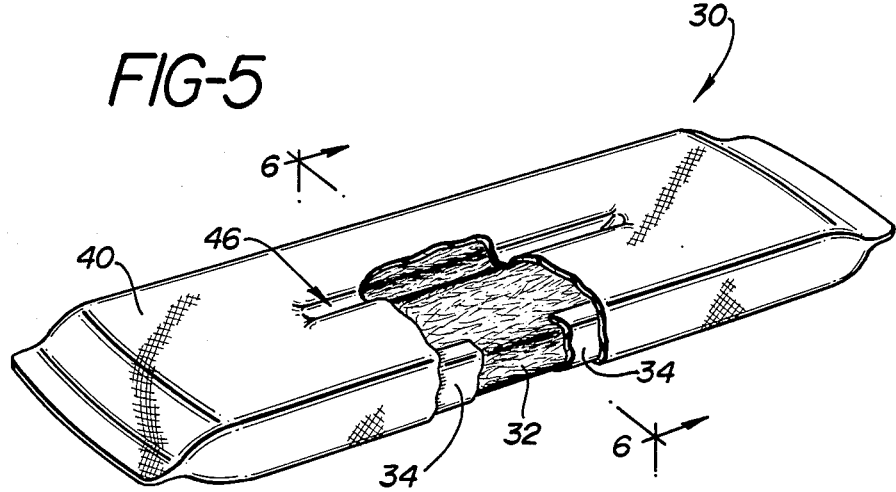
FIG. 5 is a perspective view of another napkin construction employing the teachings of this invention.
Figure 6:
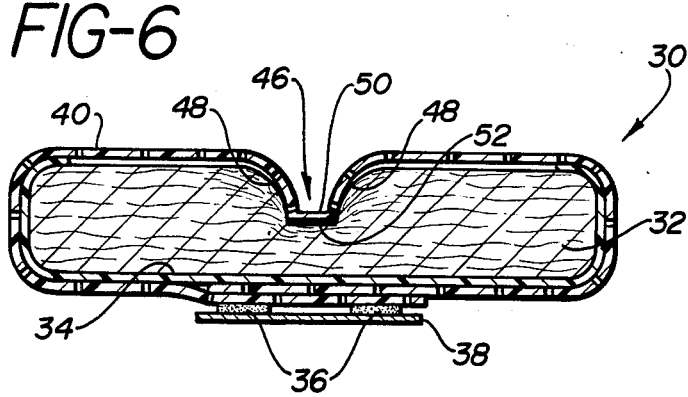
FIG. 6 is a transverse, cross sectional view of the napkin illustrated in FIG. 5.

Referring now to FIGS. 5 and 6 illustrated therein is another embodiment of this invention in an alternative sanitary napkin 30. The napkin 30 is provided with an absorbent core, pad 32. Overlying the garment facing side of the napkin is a barrier layer 34 which also overlies the longitudinal edges and, as is illustrated, may overlie a portion of the body facing side. In a manner similar to the napkin shown in FIGS. 1-4, napkin 30 is provided with adhesive elements (two) 36 for adhering the napkin to an undergarment, said adhesive elements being protected, prior to use, by a release strip 38.

A cover 40 is provided, overlying the body facing portion of the napkin and overlapping on the opposite, garment facing side, thereby completely enveloping pad 32 and barrier layer 34. This sheet is similar in its clean and dry properties to that of cover 16 shown in connection with FIGS. 1-4.

In a manner similar to that described in connection with the prior described embodiment, a channel 46 is provided in pad 32, such channel having walls 48 and a bottom 50. As best viewed in FIG. 6, and in accordance with this invention, cover 40 is positively adhered to the bottom 50 of the channel 46 using adhesive 52.

To illustrate the advantages accrued by following the teachings of this invention, the following examples are provided:

EXAMPLE 1

Sanitary napkins having the shape, construction and proportions of that illustrated in FIGS. 1-4 are prepared. The napkins all have a maximum length of about 25 cm, a minimum width of about 5 cm and a maximum thickness of about 2 cm. The pad, comprising wood pulp fluff, weighs about 9 gms and has, impressed therein, a channel which is centrally located on the body facing side of the pad, is 7.6 cm long, 0.3 cm wide, and 0.6 cm deep. The cover material utilized is a reticulated polyethylene cover such as that described in detail in copending patent application Ser. No. 632,753. The open area of such cover is 25% and 7.5% by weight of titanium dioxide is incorporated into the polyethylene to serve as an opacifying agent.

Figure 2A:
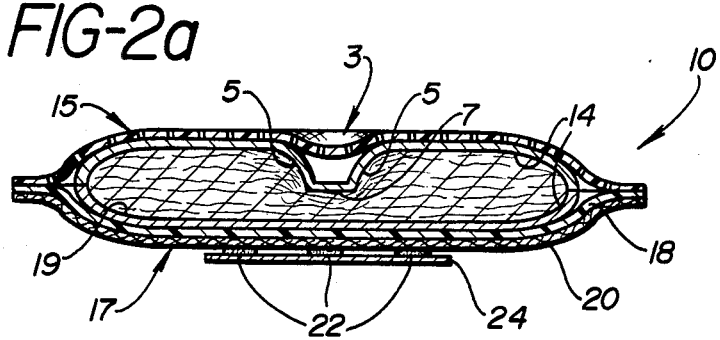
FIG. 2a is a view, similar to that of FIG. 2, but illustrating a napkin which fails to incorporate the teachings of this invention.

A first series of such napkins are constructed in accordance with one embodiment of this invention by auto heat bonding the polyethylene cover to the bottom of the channel. A second series comprises napkins wherein an attempt is made to heat bond but which attempt fails resulting in a napkin having the general configuration of that illustrated in FIG. 2a wherein identically numbered parts are identical to the elements depicted in FIG. 2. In FIG. 2a it should be noted that in contrast to the teachings of this invention, the cover 16 is not adhered to the bottom of the channel but instead spans the channel.

A third series of napkins is provided wherein the adherence of the cover to the bottom of the channel is accomplished by applying a line of hot melt adhesive designated as HM2152 by the H. B. Fuller Company and comprising generally poly(ethylene/vinylacetate). The line of adhesive is applied to the pad facing side of the cover 16 and is of a length essentially equal to that of the channel. The weight of adhesive applied is 0.006 gms. The adhesion is effected by applying heat via a male member at about 210° F.

A fourth series of napkins are prepared wherein hot melt adhesive is applied but the cover is not adhered to the bottom of the channel and hence the napkin again has the general configuration of FIG. 2a.

Finally, a fifth series of napkins are prepared, wherein no channel is present in the pad.

EXAMPLE 2

Each of the napkins described in Example 1 are tested to determine the clean and dry appearance after application of fluid. The fluid employed is an ersatz menstrual fluid composition which has salt content and surface tension characteristics of menstrual fluid and is colored to resemble the same. Each sample is placed on a glass plate with its body facing side upward. A plexiglass plate having an orifice therethrough is placed over the body facing side of the sample with the orifice being centered with respect to the napkin. The orifice is in the shape of an elipse having a major diameter (oriented longitudinally with the napkin) of 1½ inches, and a minor diameter of ¾ inches. The plate is ½ inch thick. Fifteen cubic centimeters of the ersatz menstrual fluid are applied to the napkin by maintaining the orifice filled until all the fifteen cubic centimeters of fluid has passed therethrough. The plate is then removed and a visual observation is made of the cover in the area of the channel to determine the appearance with respect to wetness. The degree of wetness is quantified by carefully wiping a preweighed rayon ball (approximately 0.5 gms) across the cover surface in the channel area, and reweighing to determine the fluid picked up by the rayon ball. Empirical evidence indicates that a visual observation will signify that the cover is wet when approximately at least 0.017 gms of moisture is present, as determined by the above-described wiping method. Less moisture will generally result in a visual observation that the cover is dry.

Table 1 below illustrates the results for the series of samples in which no channel was present.

TABLE 1

| Unchannelled Napkins | | |
|---|---|---|
| Sample Number | Cover Appearance | Fluid On Surface (g) |
| 1 | Dry | 0 |
| 2 | Dry | 0 |
| 3 | Dry | 0.006 |
| 4 | Dry | 0 |
| 5 | Dry | 0 |
| 6 | Dry | 0.004 |
| 7 | Dry | 0 |
| 8 | Dry | 0 |
| 9 | Dry | 0 |
| 10 | Dry | 0.006 |
| 11 | Dry | 0 |
| 12 | Dry | 0 |
| 13 | Dry | 0.004 |
| 14 | Dry | 0 |
| 15 | Dry | 0 |
| 16 | Dry | 0 |
| 17 | Dry | 0 |
| 18 | Dry | 0 |
| 19 | Dry | 0 |
| 20 | Dry | 0 |

The column headed "Cover Appearance" records the visual observation and the column headed "Fluid on Surface" records the results of the wipe test described above. As can be seen from this Table 1, in the absence of a channel the cover both appears and is found to be actually dry. Only negligible amounts of fluid are found on a small minority of samples.

Table 2 below illustrates the results obtained for the series of samples in which the heat bonding was ineffective and the napkin resembled that schematically illustrated in FIG. 2a.

TABLE 2

| Napkin with Nonadhered Cover | | |
|---|---|---|
| Sample Number | Cover Appearance | Fluid On Surface (g) |
| 1 | Dry | 0.0133 |
| 2 | Wet | 0.030 |
| 3 | Dry | 0.010 |
| 4 | Wet | 0.080 |

TABLE 2-continued

| Napkin with Nonadhered Cover | | |
|---|---|---|
| Sample Number | Cover Appearance | Fluid On Surface (g) |
| 5 | Wet | 0.028 |
| 6 | Wet | 0.025 |
| 7 | Wet | 0.020 |
| 8 | Wet | 0.020 |
| 9 | Wet | 0.025 |
| 10 | Wet | 0.111 |
| 11 | Wet | 0.010 |
| 12 | Dry | 0.012 |
| 13 | Wet | 0.020 |
| 14 | Wet | 0.027 |
| 15 | Dry | 0.012 |
| 16 | Wet | 0.018 |
| 17 | Wet | 0.017 |
| 18 | Wet | 0.020 |
| 19 | Wet | 0.068 |
| 20 | Wet | 0.019 |

In contrast to the napkins of Table 1, once a channel is present, the area of the cover now exhibits, in a majority of cases, a wet appearance and a substantial quantity of fluid is measured. This is true notwithstanding the fact that the same clean and dry cover material, as used in connection with the unchanneled napkin, is employed.

Table 3 below illustrates the results obtained for the series of napkins which, in accordance with the teachings of this invention, has the cover auto heat bonded to the bottom of the channel (i.e., heat bonded without addition of adhesives).

TABLE 3

| Napkin with Auto Heat Bonded Cover | | |
|---|---|---|
| Sample Number | Cover Appearance | Fluid On Surface (g) |
| 1 | Dry | 0 |
| 2 | Dry | 0 |
| 3 | Dry | 0 |
| 4 | Dry | 0 |
| 5 | Dry | 0 |
| 6 | Dry | 0 |
| 7 | Dry | 0 |
| 8 | Dry | 0 |
| 9 | Dry | 0 |
| 10 | Dry | 0 |
| 11 | Dry | 0 |
| 12 | Dry | 0 |
| 13 | Dry | 0 |
| 14 | Dry | 0 |
| 15 | Dry | 0 |
| 16 | Dry | 0 |
| 17 | Dry | 0 |
| 18 | Dry | 0 |
| 19 | Dry | 0 |
| 20 | Dry | 0 |

As can be noted from Table 3, the bonding of the cover to the bottom of the channel has cured the problem exhibited by the napkin of Table 2.

Table 4 illustrates the results obtained by testing the series of napkins wherein hot melt adhesive has been applied but the cover remains unadhered to the channel bottom.

TABLE 4

| Napkin with Unadhered Cover | | |
|---|---|---|
| Sample Number | Cover Appearance | Fluid On Surface (g) |
| 1 | Wet | 0.308 |
| 2 | Wet | 0.617 |
| 3 | Wet | 0.802 |

TABLE 4-continued

Napkin with Unadhered Cover

| Sample Number | Cover Appearance | Fluid On Surface (g) |
|---|---|---|
| 4 | Dry | 0.008 |
| 5 | Dry | 0.005 |
| 6 | Dry | 0.010 |
| 7 | Wet | 0.713 |
| 8 | Wet | 0.240 |
| 9 | Dry | 0.008 |
| 10 | Dry | 0.014 |
| 11 | Dry | 0.015 |
| 12 | Wet | 0.103 |
| 13 | Dry | 0.009 |
| 14 | Dry | 0.015 |
| 15 | Wet | 0.709 |
| 16 | Dry | 0.011 |
| 17 | Dry | 0.003 |
| 18 | Dry | 0.005 |
| 19 | Wet | 0.153 |
| 20 | Wet | 0.310 |

As can be seen from this table by failing to adhere the cover to the bottom of the channel, for essentially 50% of the samples, the cover appeared wet and for almost every sample, substantial quantities of fluid were measured.

Table 5 illustrates the results obtained from the series of napkins in which the cover is adhered to the bottom of the napkin channel using the hot melt adhesive.

TABLE 5

Napkin with Hot Melt Adhered Cover

| Sample Number | Cover Appearance | Fluid On Surface (g) |
|---|---|---|
| 1 | Dry | 0 |
| 2 | Dry | 0 |
| 3 | Dry | 0 |
| 4 | Dry | 0.005 |
| 5 | Dry | 0 |
| 6 | Dry | 0 |
| 7 | Dry | 0 |
| 8 | Dry | 0 |
| 9 | Dry | 0 |
| 10 | Dry | 0 |
| 11 | Dry | 0 |
| 12 | Dry | 0 |
| 13 | Dry | 0 |
| 14 | Dry | 0 |
| 15 | Dry | 0 |
| 16 | Dry | 0 |
| 17 | Dry | 0 |
| 18 | Dry | 0 |
| 19 | Dry | 0 |
| 20 | Dry | 0 |

In accordance with the teachings herein, this adherence has solved the problem of wetness related to the napkins of Table 4 and in every case the napkin cover appeared dry. In only one sample was any moisture detected and, in that case, to an essentially insubstantial degree.

What is claimed is:

1. A sanitary napkin comprising an elongated absorbent core having a body facing side and a garment facing side; said absorbent core having impressed into the body facing side at least one elongated channel having walls and a bottom; said napkin having a hydrophobic body fluid pervious cover comprising a continuous film of hydrophobic polymeric material rendered permeable to body fluid by being provided with apertures; said fluid pervious cover overlying said body facing side of said absorbent core including its impressed channel; said cover extending into said channel and being adhered to said channel bottom and unadhered to the remainder of said absorbent core.

2. The napkin of claim 1 wherein said cover comprises thermoplastic material and is adhered to said channel bottom by auto heat bonding.

3. The napkin of claim 2 wherein said cover comprises polyethylene and is heat bonded to said channel bottom by a male member having a maximum temperature of between 290° and 300° F. and applied for no more than 0.4 seconds.

4. The napkin of claim 1 wherein said cover is adhesively bonded to said channel bottom with an adhesive.

5. The napkin of claim 4 wherein said adhesive is an emulsion adhesive.

6. The napkin of claim 4 wherein said adhesive is a hot melt adhesive.

7. The napkin of claim 6 wherein said hot melt adhesive is adhesively active at a temperature at least 2° F. below the initial melting point of the cover.

8. The napkin of claim 7 wherein said hot melt adhesive is adhesively active at a temperature at least 4° F. below the initial melting point of the cover.

9. The napkin of claim 8 wherein said cover comprises polyethylene and said hot melt is adhesively active at a temperature below 258° F.

10. The napkin of claim 9 wherein said hot melt is adhesively active at a temperature below 256° F.

11. The napkin of claim 4 wherein said adhesive is present in the quantity of at least 0.001 grams of adhesive per linear inch of channel.

12. The napkin of claim 11 wherein said adhesive is present in the quantity of at least 0.0015 grams of adhesive per linear inch of channel.

13. The napkin of claim 11 wherein said adhesive is present in the quantity of less than 0.01 grams of adhesive per linear inch of channel.

14. The napkin of claim 1 wherein said channel extends longitudinally with said napkin for a length of at least 10% of the length of said core.

15. The napkin of claim 14 wherein said channel extends longitudinally with said napkin for a length of at least 25% of the length of said core.

* * * * *